United States Patent [19]
Day

[11] Patent Number: 5,900,233
[45] Date of Patent: May 4, 1999

[54] EPICHLOROHYDRIN AND 1-(3-AMINOPROPYL) IMIDAZOLE COPOLYMER AND ITS USE IN TREATING IRRITABLE BOWEL SYNDROME

[76] Inventor: Charles E. Day, 1434 Sunbeam Rd., Leitchfield, Ky. 42754

[21] Appl. No.: 08/951,664

[22] Filed: Oct. 16, 1997

[51] Int. Cl.$^6$ ............... A61K 31/74; A61K 9/48; A61K 9/20; A61K 47/30
[52] U.S. Cl. ............ 424/78.01; 424/451; 424/464; 514/772.3
[58] Field of Search ............... 424/400, 78.01, 424/451, 464; 514/772.3

[56] References Cited

U.S. PATENT DOCUMENTS

| | | | |
|---|---|---|---|
| 4,557,930 | 12/1985 | Kihara et al. | 424/78.01 |
| 4,777,042 | 10/1988 | Toda et al. | 424/78.01 |
| 5,380,522 | 1/1995 | Day | 424/78.08 |
| 5,624,963 | 4/1997 | Mandeville, III et al. | 514/789 |

OTHER PUBLICATIONS

Revici, *Chemical Abstracts*, vol. 108, #68958, 1988.
Nomura et al., *Chemical Abstract*, vol. 114, #30,145, 1991.
(Mit) Kihara et al., *Chemical Abstracts*, vol. 97, #203,236, 1983.
Katogi et al., *Chemical Abstracts*, vol. 127, #239,147, 1997.
Toepfl, *Chemical Abstracts*, vol. 106, #51 645 1987.
Hashim, S.A., et al., "Experimental steatorrhea induced in man by bile acid sequestrant.", Proc. Soc. Exp. Biol. Med. 106: 173–175 (1965).
Bierman EL, "Atherosclerosis and Other Forms of Arteriosclerosis." In: Harrison's Principles of Internal Medicine, 13th ed., KJ Isselbacher et al. (eds.). New York, McGraw–Hill, pp. 1106–1116 (1994).
Toda H. et al., "Bile acid binding and hypocholesteremic activity of a new anion exchange resin from 2–methylimidazol and epichlorohydrin", J. Pharm. Sci. 77:531–533 (1988).
Benson G.M. et al. "SK&F 97426–A; a novel bile acid sequestrant wih higher affinities and slower dissociation rates *in vitro* than cholestyramine"; J Pharm Sci. 86:76–81 (1997).
American Gastroenterological Association Medical Position Statement: Irritable Bowel Syndrome. Gastroenterology 112:2118–2119 (1997).
Drossman DA, Whitehead WE, Camilleri M., "Irritable bowel syndrome: a technical review for practice guideline development", Gastroenterology 112:2120–2137 (1997).
Snape WJ Jr., "Irritable bowel syndrome", In: Bockus Gastroenterology, 5th edition (W.S. Haubrich, F. Schoffner, ed.) Philadelphia: W.B. Saunders, pp. 1619–1636 (1995).
Harrison's Principles of Internal Medicine, 13th ed., K.J. Isselbacher et al. (eds). New York, McGraw–Hill, pp. 446 ff (1994).
Williams' Endocrinology, 8th ed., J.D. Wilson, D.W. Foster (eds). Philadelphia, Saunders, pp. 1335 ff. (1992).
Goodman & Gilman's, The Pharmacological Basis of Therapeutics, 9th ed., J.G. Hardman et al. (eds). New York, McGraw–Hill, pp. 875 ff (1996).

*Primary Examiner*—Carlos A. Azpuru
*Attorney, Agent, or Firm*—The Firm of Gordon W. Hueschen

[57] ABSTRACT

An anion-binding hydrophilic epichlorohydrin and 1-(3-aminopropyl)imidazole copolymeric bile acid sequestrant, pharmaceutical compositions thereof, and use thereof in the treatment of ailments or conditions in which a bile acid sequestrant and inhibitor of fat absorption is indicated.

11 Claims, No Drawings

EPICHLOROHYDRIN AND 1-(3-AMINOPROPYL) IMIDAZOLE COPOLYMER AND ITS USE IN TREATING IRRITABLE BOWEL SYNDROME

FIELD OF THE INVENTION

Bile acid sequestrants, in particular anion-binding hydrophilic copolymers, pharmaceutical compositions thereof, and their use as bile acid sequestrants.

BACKGROUND OF THE INVENTION AND PRIOR ART

Bile acid sequestrants (BAS) are a class of drugs employed chiefly as hypolipidemic agents. Each of the BAS is an anion exchanger which exerts its effect by binding bile acids and thus interfering with their recycling, or enterohepatic circulation. BAS hitherto developed have included several types of polymers. The BAS first marketed in the U.S., cholestyramine, a water-insoluble copolymer of styrene and divinylbenzene characterized by trimethylbenzylammonium groups, has a somewhat limited capacity to bind bile acids, so very large quantities (upwards of twenty (20) grams per day) must be ingested in order to achieve desired lowering of plasma LDL levels. Colestipol hydrochloride which, like cholestyramine, is currently on the market in the U.S., is a water-soluble copolymer of diethylenetriamine and 1-chloro-2,3-epoxypropane. Colestipol hydrochloride contains secondary and tertiary amino groups and its bile acid binding therefore shows a marked pH-dependence. Other BAS are disclosed in U.S. Pat. Nos. 5,624,963, 4,557,930, and 4,777,042. A quaternary alkylammonium polymethacrylate BAS with higher in vitro bile acid binding properties than cholestyramine has recently been reported (Benson G. M. et al. "SK&F 97426-A; a novel bile acid sequestrant with higher affinities and slower dissociation rates in vitro than cholestyramine"; J Pharm Sci. 86:76–81 (1997)). In U.S. Pat. Nos. 4,557,930 and 4,777,042 are described anion exchange resins (also described in Toda H. et al., "Bile acid binding and hypocholesteremic activity of a new anion exchange resin from 2-methylimidazol and epichlorohydrin", J. Pharm. Sci. 77:531–533 (1988)) having as functional groups imidazolium salts. In U.S. Pat. No. 5,624,963 are described various ion exchange resins. The inventions reported in U.S. Pat. Nos. 4,557,930, 4,777,042 and 5,624,963 do not relate to the use of 1-(3-aminopropyl) imidazole as a starting monomer for the synthesis of ion exchange resins.

Obesity can be defined as a syndrome in which a body weight higher than that which is optimally healthful is maintained. The primary cause of obesity remains elusive, but it is clear that obesity results from the expenditure of fewer calories than are ingested over a prolonged period of time. A higher-than-healthful body weight is thereafter maintained, and can lead to numerous life-threatening complications such as hypertension, insulin-resistant diabetes mellitus, and hyperlipidemias including hypercholesterolemia and, consequently, cardiovascular disease and stroke. The subject of obesity is reviewed in chapters of Williams' Endocrinology, 8th ed., J. D. Wilson, D. W. Foster (eds). Philadelphia, Saunders, pp. 1335 ff. (1992) and Harrison's Principles of Internal Medicine, 13th ed., K. J. Isselbacher et al. (eds). New York, McGraw-Hill, pp. 446 ff (1994).

It is difficult to estimate accurately the prevalence of obesity, but probably tens of millions of persons in the U.S. are obese. Indeed, some experts believe the incidence of obesity in the U.S. and in other industrialized nations is increasing. Treatment of obesity by diet, behavior modification, medication, or surgery has been in general dismally unsuccessful. Once an initial fluid-dominated weight loss is achieved, dieters find it extremely difficult if not impossible to keep weight off. Likewise, behavior modification, to alter subjects' responses to cues to overeat, has yielded uneven results at best. Despite hopes for the efficacy of a regimen of serotoninergic drugs, especially in combination with sympathomimetic agents, it is unclear whether long-term weight reduction will be achieved through such approaches. Significant morbidity and mortality have been associated with surgical procedures such as ileal resection, though gastric plication appears to succeed in eliciting weight loss in some surgical subjects. Nevertheless, an efficacious nonsurgical treatment for obesity is yet to be desired.

The tendency of a diet to promote weight gain, or to militate against weight loss, has been shown to be directly related to the diet's fat content. That is, other factors, including the total number of calories, being equal, a diet having more calories from fat, when consumed, will tend to promote weight gain more readily than its lower-fat counterpart. Hence it stands to reason that diminution of the proportion of fat in a diet available for absorption will make that diet more likely to promote weight loss.

One way to decrease fat absorption has been to inhibit lipase with a compound such as lipstatin or tetrahydrolipstatin as described in U.S. Pat. No. 5,540,917. The long-term consequences of therapy with such agents remain unclear. On the other hand, bile acid sequestrants work by binding bile acids present in the intestinal lumen which are otherwise destined to be reabsorbed along with dietary lipids and the products of their digestion. The patient's response to bile acid sequestrants as a class is well-documented and complex, involving a reduction in the amount of dietary fat absorbed from the intestinal lumen, an increase in expression of the LDL receptor on hepatocytes, and other factors. Dietary lipids must form micelles in order to be acted upon by lipases and absorbed across the intestinal epithelium. Bile acid sequestrants limit micelle formation by removing bile acids, a crucial component of such micelles. Dietary lipids are thus absorbed sparingly and instead excreted. Current medical treatment for obesity does not employ a bile acid sequestrant as an inhibitor of fat absorption, but use of a bile acid sequestrant holds promise since it achieves the same therapeutic goal as ileal resection, viz., diminution of fat absorption, without the morbidity or mortality associated with surgery. Indeed, the clinical experience with bile acid sequestrants shows them to be in general well tolerated (Goodman & Gilman's, The Pharmacological Basis of Therapeutics, 9th ed., J. G. Hardman et al. (eds). New York, McGraw-Hill, pp. 875 ff (1996)).

Thus, the removal of bile acids or bile acid salts from a patient by the employment of a bile acid sequestrant acts to inhibit the digestion or absorption of fat, acts for the treatment or prevention of obesity, and also acts as an effective prevention or treatment of hyperlipidemia, hypercholesterolemia, atherosclerosis, arteriosclerosis, coronary artery disease, and ischemic heart disease.

Irritable bowel syndrome (IBS), a chronic or recurring gastrointestinal disorder, afflicts as many as 24% of women and 19% of men in the U.S., Europe, Japan, and China. IBS produces abdominal pain or discomfort in its victims and accounts for about one-eighth of primary care and more than one-fourth of gastroenterology practice. IBS has tremendous societal and economic impact since persons with IBS symptoms miss three times as many work days as those without and incur 70% higher health care costs. The American Gastroenterological Association has recently underscored the importance of IBS by issuing both a position statement (American Gastroenterological Association Medical Position Statement: Irritable Bowel Syndrome. Gastroenterology 112:2118–2119 (1997)) and a technical review (Drossman D A, Whitehead W E, Camilleri M., "Irritable bowel syndrome: a technical review for practice guideline development", Gastroenterology 112:2120–2137 (1997)) on IBS. The description herein of IBS is based chiefly on these documents and on other current literature (such as that reviewed in Snape W J Jr., "Irritable bowel syndrome", In: Bockus Gastroenterology, 5th edition (W. S. Haubrich, F. Schoffner, ed.) Philadelphia: W. B. Saunders, pp. 1619–1636 (1995)).

IBS presents itself as abdominal pain accompanied by altered bowel habits. There is no established biological marker for IBS, which appears to result from faulty regulation in both the gastrointestinal and nervous systems. Once clinicians rule out other possible causes of IBS symptoms, they must devise a treatment plan based upon the severity and nature of the symptoms as well as other factors such as the degree of impairment the individual is experiencing in the activities of daily living. At present, treatment options range from education and dietary modification to drug therapy to psychological therapy. Drug and/or psychological therapy is called for in those 30% of IBS patients with moderate or severe symptoms. Given an IBS prevalence of 19% to 24%, IBS sufferers requiring such therapy represent 6–7% of the population at large, or well over 100 million individuals in continual need of such therapy in the U.S., Europe, Japan, and China.

The AGA position statement recommends antispasmodic (anticholinergic) medication for IBS pain and bloating, or a tricyclic antidepressant or serotonin-selective reuptake inhibitor if the pain is severe. Dietary fiber is recommended (cisapride is also mentioned) for IBS constipation, whereas loperamide is recommended for diarrhea. For treatment of IBS patients presented with predominant diarrhea, the bile acid sequestrant "[c]holestyramine may be considered for a subgroup of patients with cholecystectomy or who may have idiopathic bile acid malabsorption." Clearly, there is no single pharmacologic treatment appropriate to all IBS sufferers. However, it is equally clear that it is acceptable clinical practice to employ a bile acid sequestrant to treat diarrhea associated with IBS.

The technical review issued by the AGA states that treatment with the bile acid sequestrant "[c]holestyramine should be considered in patients with IBS who have predominant diarrhea." Cholestyramine, a copolymer of styrene and divinylbenzene possessing trimethylbenzylammonium groups, has a somewhat limited capacity to bind bile acids, so very large quantities (as much as 20 grams per day) must be ingested in order to alleviate symptoms.

According to the present invention, the prevention of diarrhea, constipation, dumping syndrome, and irritable bowel syndrome, and pain aspects or symptoms thereof, are also ailments which may be treated or prevented by the employment of a bile acid sequestrant, and in particular the novel bile acid sequestrant of the present invention, which operates in the manner disclosed in my prior U.S. Pat. No. 5,380,522 for the treatment or prevention of IBS, using in that case a combination of polymeric substances comprising as essential components anion binding and hydrophilic polymers or chitosan, which acts as both. The present invention, involving as it does an entirely novel anion-binding polymer which is also hydrophilic, can be readily employed for the same purpose and to the same end.

THE PRESENT INVENTION

The present invention relates to a novel anion-binding hydrophilic epichlorohydrin (ECH) and 1-(3-aminopropyl) imidazole (API) copolymeric bile acid sequestrant (sometimes referred to for convenience as A-2497), pharmaceutical compositions thereof, and the use thereof for all of the foregoing purposes for which a bile acid sequestrant is presently recommended, namely, for the purpose of removing bile acids or bile acid salts from a patient, for inhibiting the digestion or absorption of fat in a patient, for treating or preventing diarrhea, constipation, dumping syndrome, or irritable bowel syndrome, and pain aspects or symptoms thereof, in a patient, for treating or preventing obesity in a patient, and for treating or preventing hyperlipidemia, hypercholesterolemia, atherosclerosis, arteriosclerosis, coronary artery disease, or ischemic heart disease in a living animal body, and especially in a human patient.

Attempts were made to prepare an insoluble, hydrophilic, anion-binding polymer from the reaction as described herein of ECH with each of the following compounds: L-histidine; L-histidine methyl ester; histamine; 2-aminoimidazole; 2-imidazolecarboxaldehyde; 2-imidazolethiol; 4-amino-5-imidazolecarboxamide. 4,5-dicyanoimidazole; 2-methyl-5-nitroimidazole; 2-mercapto-1-methylimidazole; 2-methylthio-2-imidazoline; 2-hydrazino-2-imidazoline; 2,2'-bis(4,5-dimethylimidazole); 1-vinylimidazole. ECH did not react with any of the aforementioned compounds to form an insoluble copolymer when mixed at a 1:1 molar ratio.

In brief, it would not be obvious to one skilled in the art to which this invention pertains that: (a) when mixed at a molar ratio of 1:1, ECH reacts with none of the imidazole compounds enumerated in the preceding paragraph to yield an insoluble copolymer; (b) when mixed at a molar ratio of 0.95:1 to 1.5:1, ECH and API react to form an insoluble hydrophilic copolymer which shows considerable capacity to bind bile acids; (c) bile acid binding in the presently-described copolymer of ECH and API varies nonmonotonically according to the molar ratio of ECH to API; (d) in a series of ECH-API copolymers, maximal bile acid binding is evinced by the polymer prepared by mixing ECH and API at a molar ratio about 1:1. Such bile acid binding averaging 1.45 mg per mg dry weight of polymer (equal to 3.7 mmol/g of bile acid) is substantial and compares favorably with that reported (2.5–4 mmol/g of bile acid) for recently-developed bile acid sequestrants, e.g., SK&F 97426-A (Benson et al. 1997).

OBJECTS OF THE INVENTION

It is an object of the present invention to provide the novel insoluble hydrophilic anion-binding epichlorohydrin and 1-(3-aminopropyl)imidazole copolymeric bile acid sequestrant, pharmaceutical compositions thereof, and use thereof for all of the foregoing enumerated indications. Additional objects of the invention will be obvious to one skilled in the art, and still further objects of the invention will become apparent hereinafter.

SUMMARY OF THE INVENTION

What I believe to be my invention, then, inter alia, comprises the following, singly or in combination:

A composition of matter which is a water-insoluble copolymer of 1-(3-aminopropyl)imidazole and epichlorohydrin; such a composition wherein the molar ratio of epichlorohydrin to 1-(3-aminopropyl)imidazole is between about 0.95:1 and about 1.5:1; and such a composition wherein the molar ratio of epichlorohydrin to 1-(3-aminopropyl)imidazole is about 1:1.

Also, a composition comprising a water-insoluble copolymer resulting from a process comprising the steps of:

mixing 1-(3-aminopropyl)imidazole with water to form a first mixture;

adding epichlorohydrin to said first mixture to form a second mixture;

heating said second mixture of 1-(3-aminopropyl) imidazole, water, and epichlorohydrin; and cooling said heated second mixture, and a process for preparing a water-insoluble copolymer of 1-(3-aminopropyl)imidazole and epichlorohydrin comprising the following steps:

mixing 1-(3-aminopropyl)imidazole with water to form a first mixture;

adding epichlorohydrin to said first mixture to form a second mixture wherein the molar ratio of epichlorohydrin to 1-(3-aminopropyl)imidazole is between about 0.95:1 and about 1.5:1;

heating said second mixture of 1-(3-aminopropyl) imidazole, water, and epichlorohydrin; and cooling said heated second mixture to produce the desired copolymer.

Further, a pharmaceutical composition comprising such a copolymer together with a pharmaceutically-acceptable carrier or diluent.

Moreover, a method for removing bile acids or bile salts from a living animal body comprising the step of orally administering to said living animal body an effective amount of such a copolymer, as well as such a method for inhibiting the digestion or absorption of fat in a living animal body; such a method for treating or preventing diarrhea, constipation, dumping syndrome, or irritable bowel syndrome, and pain aspects or symptoms thereof, in a living animal body; such a method for treating or preventing hyperlipidemia, hypercholesterolemia, atherosclerosis, arteriosclerosis, coronary artery disease, or ischemic heart disease in a living animal body; and such a method for treating or preventing obesity in a living animal body.

DETAILED DESCRIPTION OF THE INVENTION

The following Examples are given by way of illustration only, and are not to be construed as limiting.

EXAMPLE 1

1:1 Molar Ratio of ECH and API

The polymer was originally synthesized at a 1:1 molar ratio of reacting monomers. Thus, 3.2 grams of 1-(3-aminopropyl)imidazole was mixed with 5.0 mL distilled water in a wide-mouthed, screw-capped 120 mL reaction vessel. To this mixture was added 2.0 mL of epichlorohydrin dropwise with stirring at room temperature. The reaction vessel was capped with a Teflon-lined lid and placed in an oven at 90 degrees C. for about twelve hours. After removal from the oven and cooling to room temperature, the firm, sliceable and friable gel was crumbled into fine particles by crushing with a flat metal spatula. The minced gel was transferred to a larger glass container and mixed with 1 L of distilled water on a magnetic stirrer. The gel particles were allowed to settle by gravity and the aqueous supernatant aspirated. The polymeric gel was then washed twice more with one-liter portions of distilled water, and the volume of the gel recorded after the last wash. The gel was then filtered and allowed to drain on absorbent paper in a drying oven at 60 degrees C. The polymeric gel thus prepared was found to possess a hydrated volume of 26 mL/g and to bind 1.20 mg bile acid (sodium chenodeoxycholate) per mg dry weight of polymer.

EXAMPLE 2

Additional Examples

Molar Ratio of about 1:1

Additional lots of the polymer were prepared and characterized.

The first additional lot possessed a hydrated volume of 49 mL/g, showed bile acid binding of 1.78 mg/mg, and gave a yield of 66% of theoretical total.

The second additional lot possessed a hydrated volume of 136 mL/g, showed bile acid binding of 1.48 mg/mg, and gave a yield of 48% of theoretical total.

The third additional lot possessed a hydrated volume of 47 mL/g, showed bile acid binding of 1.35 mg/mg, and gave a yield of 57% of theoretical total.

On average, then, prepared polymer at a 1:1 molar ratio possessed a hydrated volume of 64 mL/g, exhibited bile acid binding of 1.45 mg/mg, and gave a yield of 57% of theoretical total.

EXAMPLE 3

Additional Examples

Molar Variation of ECH:API of 0.95 to 1.50 to 1

Additional lots of the polymer were prepared. The reaction was altered by varying the molar ratio (epichlorohydrin to 1-(3-aminopropyl)imidazole) of the reacting monomers. Hydrated volume varied inversely according to the molar ratio of reacting monomers. Bile acid binding varied non-monotonically according to the molar ratio of the reacting monomers.

For a first additional example, at a molar ratio of ECH:API of 0.95, hydrated volume was 378 mL/g, bile acid binding was 1.35 mg/mg, and the yield of product was 27% of theoretical total.

For another additional example, at a molar ratio of ECH:API of 1.05, hydrated volume was 21 mL/g, bile acid binding was 1.90 mg/mg, and the yield of product was 76% of theoretical total.

For yet another additional example, at a molar ratio of ECH:API of 1.125, hydrated volume was 13 mL/g, bile acid binding was 0.91 mg/mg, and the yield of product was 81% of theoretical total.

For still another additional example, at a molar ratio of ECH:API of 1.25, hydrated volume was 6 mL/g, bile acid binding was 0.82 mg/mg, and the yield of product was 88% of theoretical total.

As a final additional example, at a molar ratio of ECH:API of 1.50, hydrated volume was 3 mL/g, bile acid binding was 0.65 mg/mg, and the yield of product was 95% of theoretical total.

BILE ACID BINDING ASSAY

The following procedure was employed to determine the bile acid binding of the ECH:API copolymers of the present invention and the foregoing examples:

Into each of several glass test tubes (13×100 mm) is weighed 10 mg of dry, finely ground polymer. To the dried polymer is added with mixing an appropriate volume (usually in the range of 0.2 to 1.0 ml) of 2.0% sodium chenodeoxycholate in 0.05M $NaHCO_3$ plus 0.1M NaCl solution. Total volume for each tube is adjusted to 3.0 ml with the same bicarbonate buffer used to make the bile acid solution. After capping, each tube is placed on an aliquot mixer, which mixes by inversion, and placed in an incubator at 37° C. for 2 hrs. After the 2 hr incubation, tubes are centrifuged, if necessary, and supernatant decanted into a clean dry tube. Each supernatant is tested for the presence of bile acid by an appropriate assay. For these assays, 0.5 ml of the tested copolymer solution which precipitates bile acids was added to each tube, and the optical density was measured at 600 nm.

From the curves generated in the above assay, the amount of bile acid bound by each polymer preparation can be readily calculated.

Since what is bound in this assay is the chenodeoxycholate anion, having a formula weight of 391.51, a 1.45 mg bound per mg of polymer represents 3.7 mmol bile acid bound per gram.

By way of further explanation, the more bile acid remaining in the supernatant, the higher the optical density at 600 nm. Thus, the assay employed is a standard assay, there being a direct relationship between the concentration of bile acid remaining unbound in the supernatant and the optical density at 600 nm.

PHARMACOLOGY

From the foregoing, it is apparent that the novel anion-binding hydrophilic epichlorohydrin and 1-(3-aminopropyl) imidazole copolymeric bile acid sequestrant of the present invention exhibits a high order of bile acid binding or sequestering activity or capacity and that, as such, it is useful in the treatment or prevention of such conditions or ailments in which the employment of such an agent, acting to remove bile acids or bile acid salts and thus also as an inhibitor of fat absorption, is indicated. The product, alone or in combination with the usual pharmaceutical diluents or excipients, is administered orally to the living animal body, e.g., patient, in amounts and dosage regimens which may approximate those presently employed for cholestyramine or colestipol hydrochloride and generally the dosages will be somewhat lower due to the superior bile acid or bile acid salt binding or sequestering capacity of the copolymer of the present invention.

Indications for which the product may be employed are therefore as cited in the foregoing, namely, for removing bile acids or bile salts from the patient, or inhibiting the digestion or absorption of fat in a patient, for treating or preventing obesity in a patient, for treating hyperlipidemia, hypercholesterolemia, atherosclerosis, arteriosclerosis, coronary artery disease, or ischemic heart disease in a patient, or for treating or preventing diarrhea, constipation, dumping syndrome, or irritable bowel syndrome, and the pain aspects or symptoms thereof, in a patient, all because of the hydrophilic nature and superior bile acid binding or sequestering activity of the copolymer of the present invention and its consequent effectiveness as an inhibitor of fat absorption.

Dosages employed may range from one gram per dose to 24 grams per dose, and the dosage regimen may be one or more dosages per day, advantageously at least prior to breakfast, but also prior to both breakfast and bedtime, or in other equal or unequal dosages spaced throughout the day, for example three times daily, the unit dosages to be determined by the number of oral applications involved per day and to be according to the prescribed regimen and directions of the physician or veterinarian in charge. Where a pharmaceutically-acceptable diluent or excipient is required or desired, this may conveniently be any suitable pharmaceutically-acceptable excipient or diluent, such as lactose, water, flavoring, or the like, according to the practice of the art.

In each case, the treatment is found to be effective in the prevention, amelioration, alleviation, or elimination of the targeted condition or ailment involved, and especially in the elimination or amelioration of irritable bowel syndrome symptoms, including the usual attendant diarrhea, constipation, and pain. A convenient mode of administration is to provide the polymer in the form of a dry powder which may be conveniently dispersed or suspended in a few ounces of fluid, for example, water, just prior to oral ingestion to facilitate administration and excessive "mouth-feel" which could interfere with patient compliance.

As will immediately be recognized by one skilled in the art, particularly after considering the disclosure of my prior U.S. Pat. No. 5,380,522, it is the bile-acid binding activity of the polymer of the present invention coupled with its hydrophilicity which makes it such an effective agent in the treatment of irritable bowel syndrome and its effective elimination of diarrhea, constipation, and pain, and it is the bile-acid binding activity of the polymer of the invention which makes it effective in the treatment or prevention of obesity, since it interferes with the absorption of fats, just as does the use of a lipase inhibitor such as lipstatin or tetrahydrolipstatin, since a bile acid sequestrant is an indirect inhibitor of lipase due to the fact that the bile acid sequestrants remove the bile acids required for micelle formation and necessary for lipase action and the lipase is therefore prevented from working, fat is not digested, and so fat is also not absorbed. Other bile acid sequestrants, such as cholestyramine, for example, have been shown to interfere with fat absorption as indicated in the reference Hashim, S. A., et al., "Experimental steatorrhea induced in man by bile acid sequestrant.", Proc. Soc. Exp. Biol. Med. 106: 173–175 (1965).

Again, just like cholestyramine, the polymer of the present invention possesses bile-acid binding activity which permits it to be effective in the treatment or prevention of various cardiovascular ailments. Bile acid sequestrants such as cholestyramine and colestipol are known to be effective in treating hyperlipidemia and their use is acknowledged as reducing the risk of ischemic heart disease, cholestyramine and colestipol being listed among the known bile acid sequestrants available for such use. Hypercholesterolemia is a more particular type of hyperlipidemia which is treated by the employment of bile acid sequestrants, whereas atherosclerosis is a more particular type of arteriosclerosis underlying coronary artery disease, which is also called ischemic heart disease and one publication evidencing the foregoing is Bierman E L, "Atherosclerosis and Other Forms of Arteriosclerosis." In: Harrison's Principles of Internal Medicine, 13th ed., K J Isselbacher et al. (eds.). New York, McGraw-Hill, pp. 1106–1116 (1994).

It is therefore seen that the present invention provides a novel and effective polymer, pharmaceutical composition, and method of treating and preventing the foregoing ailments or conditions which are subject to improvement by the provision of a bile acid binder or sequestrant, which acts also as an inhibitor of fat absorption, in effective amounts, and in any case orally administered, all having the unpredictable and highly advantageous characteristics and effects and results as more fully set forth in the foregoing, and whereby all of the objectives of the present invention are attained.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

I claim:

1. A composition of matter which is a water-insoluble copolymer of epichlorohydrin and 1-(3-aminopropyl) imidazole, wherein the molar ratio is at least 0.95:1.

2. The composition of claim 1, wherein the molar ratio of epichlorohydrin to 1-(3-aminopropyl)imidazole is between about 0.95:1 and about 1.5:1.

3. The composition of claim 2, wherein the molar ratio of epichlorohydrin to 1-(3-aminopropyl)imidazole is about 1:1.

4. A composition comprising a water-insoluble copolymer resulting from a process comprising the steps of:

mixing 1-(3-aminopropyl)imidazole with water to form a first mixture;

adding epichlorohydrin to said first mixture to form a second mixture;

heating said second mixture of 1-(3-aminopropyl) imidazole, water, and epichlorohydrin; and cooling said heated second mixture.

5. A process for preparing a water-insoluble copolymer of 1-(3-aminopropyl)imidazole and epichlorohydrin comprising the following steps:

mixing 1-(3-aminopropyl)imidazole with water to form a first mixture;

adding epichlorohydrin to said first mixture to form a second mixture wherein the molar ratio of epichlorohydrin to 1-(3-aminopropyl)imidazole is between about 0.95:1 and about 1.5:1;

heating said second mixture of 1-(3-aminopropyl) imidazole, water, and epichlorohydrin; and cooling said heated second mixture to produce the desired copolymer.

6. A pharmaceutical composition comprising the water-insoluble copolymer of claim 1 together with a pharmaceutically-acceptable carrier or diluent.

7. A pharmaceutical composition comprising the water-insoluble copolymer of claim 2 together with a pharmaceutically-acceptable carrier or diluent.

8. A pharmaceutical composition comprising the water-insoluble copolymer of claim 3 together with a pharmaceutically-acceptable carrier or diluent.

9. The method for treating or preventing diarrhea, constipation, dumping syndrome, or irritable bowel syndrome, and symptoms thereof, in a living animal body, comprising the step of orally administering to said living animal body an effective amount of the water-insoluble copolymer according to claim 1.

10. The method for treating or preventing diarrhea, constipation, dumping syndrome, or irritable bowel syndrome, and symptoms thereof, in a living animal body, comprising the step of orally administering to said living animal body an effective amount of the water-insoluble copolymer according to claim 2.

11. The method for treating or preventing diarrhea, constipation, dumping syndrome, or irritable bowel syndrome, and symptoms thereof, in a living animal body, comprising the step of orally administering to said living animal body an effective amount of the water-insoluble copolymer according to claim 3.

* * * * *